United States Patent [19]

Gokel

[11] 4,436,664

[45] Mar. 13, 1984

[54] NITROGEN-CONTAINING POLYETHER MACROCYCLES WITH A SIDEARM CONTAINING NEUTRAL ELECTRON DONOR GROUPS

[75] Inventor: George W. Gokel, Greenbelt, Md.

[73] Assignee: W. R. Grace & Co., New York, N.Y.

[21] Appl. No.: 339,530

[22] Filed: Jan. 15, 1982

Related U.S. Application Data

[63] Continuation-in-part of Ser. No. 203,165, Nov. 3, 1980, abandoned, which is a continuation-in-part of Ser. No. 198,981, Oct. 21, 1980, abandoned.

[51] Int. Cl.$^3$ ............................................. C07D 273/01
[52] U.S. Cl. ............................................. 260/330.6
[58] Field of Search ............................. 260/338, 330.6

[56] References Cited

U.S. PATENT DOCUMENTS 4,256,859  3/1981  Woo ................................. 260/338 X

FOREIGN PATENT DOCUMENTS 2153844  6/1972  Fed. Rep. of Germany .

OTHER PUBLICATIONS

C.A., 87(1977), 87:39444u, Gokel, et al.
C.A., 89(1978), 89:216801x, Dix, et al.
C.A., 91(1979), 91:123721x, Johnson, et al.
C.A., 93(1980), 93:65419h, Voegtle, et al.
C.A., 92(1980), 92:181239c, Okahara, et al.
C.A., 93(1980), 93:7439d, Dix, et al.
Dix et al., Chem. Ber., 113, (1980), pp. 457–470.
C.A., 89(1978), 89:197505k, Ping—Lin, et al.

*Primary Examiner*—Joseph Paul Brust
*Attorney, Agent, or Firm*—Richard P. Plunkett; William W. McDowell, Jr.

[57] ABSTRACT

This invention relates to novel crown ether compositions which have been given the cognomen "lariat ethers". They have been designed with one or more arms bearing neutral donor groups capable of interacting with a complexed metal ion and thereby affording enhanced cation binding compared to simple crown ethers. Evidence of enhanced cation binding has been obtained and the compounds have also shown utility as phase transfer catalysts.

12 Claims, 1 Drawing Figure

U.S. Patent    Mar. 13, 1984    4,436,664
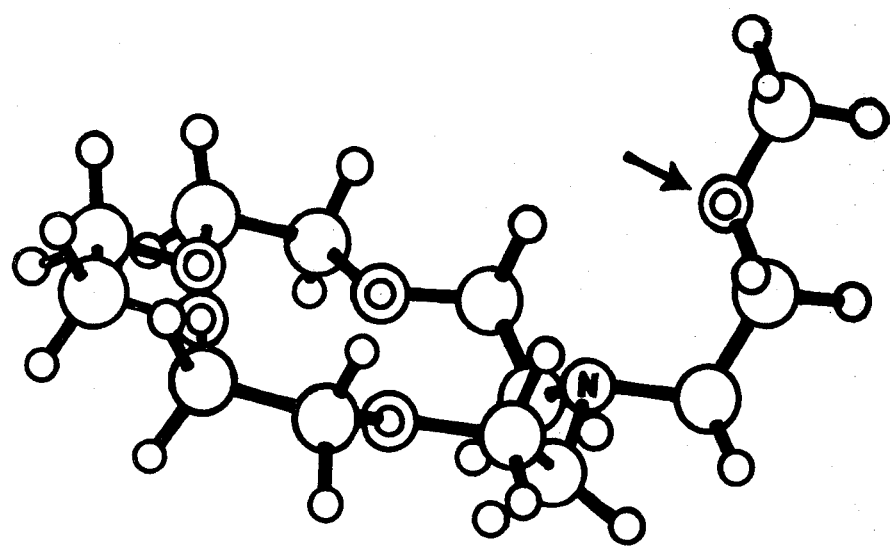
○ = C
◎ = O
Ⓝ = N

NITROGEN-CONTAINING POLYETHER MACROCYCLES WITH A SIDEARM CONTAINING NEUTRAL ELECTRON DONOR GROUPSsp

This application is a continuation-in-part of my copending application having Ser. No. 203,165, filed Nov. 3, 1980, now abandoned, which in turn is a continuation-in-part of application having Ser. No. 198,981, filed Oct. 21, 1980, now abandoned.

This invention relates to novel crown ether compositions which have been given the cognomen "lariat ethers." They have been designed to contain a macrocyclic polyether ring as found in simple crown ethers, but are substituted by a sidearm bearing a neutral Lewis basic donor group such as oxygen or nitrogen. The aforementioned donor group must be at a distance from the macroring such that a metallic cation complexed in the ring will be within bonding (solvating) distance of the donor group. Whereas crown ethers complex cations by enveloping them in a two-dimensional matrix of donor groups, the sidearm of the lariat ether can reach over and solvate from above, adding a three-dimensional component of solvation to the complex. The concept of roping and tying an animal with a lasso suggests the name "lariat ether" since the ring binds the cation and further stabilization is provided by the sidearm donor group. The name "lariat" comes from the Spanish, la reata=the rope.

BACKGROUND OF THE INVENTION

1. Field of the Invention

This invention relates to new macrocyclic polyether compositions and to complexation of ionic metal compounds therewith.

2. Description of the Prior Art

The complexation of metallic cations by macrocyclic (crown) polyethers was first demonstrated by Pedersen (*J. Amer. Chem. Soc.*, 1967, 87, 7017). Since his original disclosure numerous polyether compounds have been prepared and reported. There has been particular interest in substituted crown polyethers in recent years, due to the possibility of anchoring such polyethers to polymer matrices. Notable among these examples are the work of Montanari (*Tetrahedron Letters,* 1979, 5550) and Woo (U.S. Pat. No. 4,256,859). These reports deal with crown compounds bearing sidearms designed to assist in appending the crown ether from a polymer matrix or backbone. Numerous others have reported similar efforts (see, for example, Okahara et al., *J. Org. Chem.,* 1980, 45, 5355). The common feature of all of the compounds described in these reports is that the arm is designed either to enhance the lipophilicity of the crown or to allow for binding of the macroring to a polymer. In no case is any additional binding anticipated from or imputed to these substituted crowns by virtue of sidearm donor interaction.

Macrocyclic compounds containing one or more nitrogen atoms are well known as noted above; see Okahara, supra. However, nitrogen lariats in which an arm capable of providing secondary solvation to the ring-bound cation is appended to the heterocyclic nitrogen have not been reported.

DESCRIPTION OF THE INVENTION

The compounds claimed herein have structures represented by the formula:

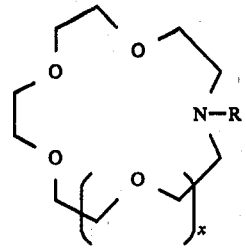

where x is 0, 1 or 2 and R is 2-(alkoxy)$_q$alkyl, 2-(alkoxy)$_q$aryl, 2-(alkoxy)$_q$aralkyl, wherein q is 1–4, aminoalkyl or aminoaryl in which the amino groups are selected from the following structures:

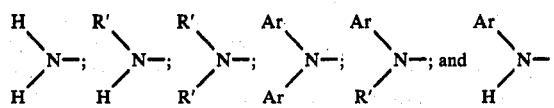

wherein R' is an alkyl group and Ar is an aryl group. All of the above mentioned alkyl groups are independently selected from alkyl containing 1–12 carbon atoms, and all aryl groups are independently selected from carbocyclic aryl groups.

Examples of 2-(alkoxy)$_q$aryl include, but are not limited to, 2-methoxyphenyl; 2,3-, 2,4-, 2,5- and 2,6-dimethoxyphenyl; 2,4,6-trimethoxyphenyl; 2-ethoxyphenyl and 2-methoxy-4-propylphenyl. Examples of 2-(alkoxy)$_q$-aralkyl in the R position include, but are not limited to, 2-methoxybenzyl; 2,6-dimethoxybenzyl; 2,6-dimethoxy-4-propylbenzyl; 2-(2-propoxyphenyl)ethyl and the like. Examples of (alkoxy)$_q$alkyl in the R position include 2-methoxyethyl; 2-methoxypropyl; 2-[2-(2-methoxyethoxy)-ethoxy]ethyl and the like. Examples of aminoalkyl in the R position include 2-aminoethyl; 3-(N-methylamino)propyl-; 2-(N,N-dimethylamino)ethyl and 2-(N,N-dimethylamino)-propyl. Examples of aminoaryl in the R position include 2-aminophenyl; 2-N-ethylaminophenyl; 2-N,N-dimethylaminophenyl and the like.

These nitrogen lariats designed to exhibit enhanced ion binding have ethyleneoxy sidechains attached to the macroring at a flexible nitrogen atom. The ring nitrogen probably contributes little to the actual binding, but this is more than compensated by the the secondary donor group(s) in the sidearm. An ORTEP drawing of N-2-methoxyethylmonoaza-15-crown-5 is shown as FIG. I. The computer generated drawing has been energy minimized for ring conformations and the sidearm is arbitrarily turned upward so that the secondary donor atom is clearly visible. An arrow points to it.

VERIFICATION OF THE LARIAT ETHER CONCEPT a. Extraction Constants

It is well known from the work of Pedersen and Frensdorff (*Angew. Chem. Int. Ed. Engl.,* 1972, 11, 46) that the association between a metallic cation and an anion can be assessed by the ability of a crown to transport M$^+$ picrate$^-$ (M=Na, K) from aqueous to organic media. Sodium and potassium picrate are insoluble in such organic solvents as CH$_2$Cl$_2$ but are readily soluble in water. When a solution of either sodium or potassium picrate is shaken with a solution of crown in dichloromethane, the crown complexes the cation and extracts it into the organic phase. The yellow picrate anion accompanies the crown-cation complex rendering the organic phase yellow. Colorimetric determination (by ultraviolet spectroscopy) allows a comparison to be made of the complexing ability of various crowns.

The so-called "extraction constants" are given as the percentage of available salt (in the aqueous phase) extracted into the organic phase.

b. Equilibrium Binding or Stability Constants, Ks.

The ability of a ligand to bind a cation can also be expressed as the stability of the resulting complex. This is an equilibrium relationship and is measured in homogeneous solution. It is important to note that the stability constants are determined in very polar solvents like 90% methanol whereas the extraction constants reflect the stability of the ligand-cation complex in a nonpolar solution like dichloromethane. We have shown that the equilibrium constant for the reaction between 15-crown-5 and sodium cation is more than 25 times higher in methanol than it is in water although both are quite polar solvents (Dishong and Gokel, *J. Org. Chem.*, 1982, 47, 147).

The binding or stability constants reported here were measured electrochemically. The conductivity of a solution of salt in the chosen solvent was determined relative to a standard calomel electrode. Ligand was then added and, after allowing time for equilibration, the conductivity was measured using an ion selective electrode as before. The difference in conductivity is proportional to the binding strength and can be related mathematically to the equilibrium constant, given in equation (1):

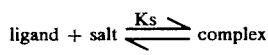

The equilibrium binding constants were, of necessity, measured in polar solvents which could dissolve the salt in the absence of the ligand. As a result the equilibrium constants, Ks, and the extraction constants (see above) are not directly comparable although they give similar information.

Note that all of the compounds which seem to give enhanced binding (see TABLE I) have a heteroatom in a position to afford secondary solvation to a ring-bound cation:

TABLE I

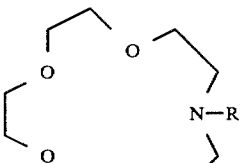

| | Ks (Na+ in MeOH) |
|---|---|
| x = 1 | |
| 1. CH₃ | 2,455 |
| 2. CH₂CH₂OCH₃ | 8,511 |
| 3. (CH₂CH₂O)₂CH₃ | 34,673 |
| 4. (CH₂CH₂O)₃CH₃ | 20,983 |
| 5. (CH₂CH₂O)₄CH₃ | 14,125 |
| x = 2 | |
| 6. CH₃ | 8,511 |

TABLE I-continued

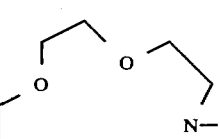

| | Ks (Na+ in MeOH) |
|---|---|
| 7. CH₂CH₂OCH₃ | 38,019 |
| 8. (CH₂CH₂O)₂CH₃ | 21,340 |
| 9. (CH₂CH₂O)₃CH₃ | 19,055 |
| 10. (CH₂CH₂O)₄CH₃ | 18,621 |

Compounds with nitrogen linked sidearms are apparently far more flexible molecules than are those in which the point of attachment is carbon. This is true to such an extent that the equilibrium binding constants (Ks values) are nearly the same for the compounds which contain identical numbers of oxygens, irrespective of whether a fifteen- or eighteen-membered ring is present. The Ks value for these highly flexible systems are substantially higher than are binding constants for even the best of the carbon-based lariat ethers.

In the group of compounds where x=0 sodium cation binding was not determined. These compounds are of potential interest as transition metal binders. Transition metals, because of their higher charges, typically have smaller ionic diameters than alkali metal cations and, therefore, presumably require smaller rings for binding them. For example, the ionic diameters of lithium, sodium, potassium, zinc (II) and cobalt (II) ions are, respectively, 1.20, 1.90, 2.66, 1.48 and 1.40 Angstroms. Even lead cation (plumbic, Pb$^{IV}$) has an ionic diameter of only 1.68 Angstroms despite the fact that it has atomic number 80.

The twelve-membered rings were designed on the same principle as that disclosed above, viz., that the macroring would provide primary solvation for the cation and the sidearm donor group would provide secondary solvation from above (i.e., axially). Synthesis of these novel crown ether compounds was accomplished according to the method of Dale (*Chem. Commun.*, 1981, 684) as shown in the equation below:

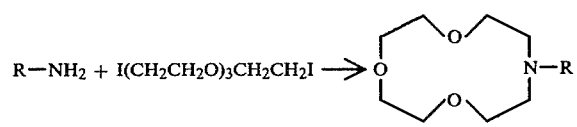

Evidence for the ability of these compounds to bind cobalt (II) nitrate was obtained by either ultraviolet spectroscopy or nuclear magnetic resonance analysis. In the former case a shift of the cobalt nitrate absorption spectrum in the presence of the ligand was taken as evidence of complexation. Line-broading of the ligands H-NMR spectrum in the presence of salt was taken as evidence of complexation when using this technique.

EXAMPLE 1

N-Allyldiethanolamine Preparation

A one liter, 3-necked, round bottomed flask, equipped with mechanical stirrer, dry ice condenser, thermometer and addition funnel (mounted atop condenser), was charged with diethanolamine (210.3 g, 2.0 mol). Finely ground sodium carbonate (17 g, 1.1 mol) was added to the flask. The amine was heated and stirred at 80° and the sodium carbonate dissolved. Allyl chloride (168.3 g, 2.2 mol) was added dropwise while keeping the reflux rate low and the temperature between 100° and 110° C. for between 2 and 3 hours. Stirring was continued at about 100° for 12 hours. The reaction mixture was allowed to cool and then diluted with dichloromethane (500 mL). The reaction mixture was then filtered. The residual salts in the reaction vessel were slurried with dichloromethane and filtered and finally all the salts were rinsed again with dichloromethane. The solvent was evaporated under reduced pressure to yield N-allyldiethanolamine (297.7 g, 102%) as a clear yellow oil. After cooling there was additional salt precipitation although the weight recorded was 297 g. Gas chromatographic analysis indicated that the product was approximately 90% pure. Distillation of the nearly pure material was conducted using a simple distillation head. Product boiling between 96° and 100° at 0.05 mL was collected affording 238 g (82% of the pure product):

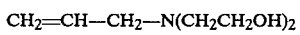

$$CH_2=CH-CH_2-N(CH_2CH_2OH)_2$$

EXAMPLE 2

Tetraethylene Glycol Dimesylate Preparation

A 5,000 mL, 3-necked flask equipped with a mechanical stirrer, thermometer and 500 mL addition funnel was charged with tetraethylene glycol (388 g, 2.0 mol) dichloromethane (1,500 mL) and triethylamine (445 g, 4.40 mol). The mixture was stirred and cooled to ca. 5° C., and methanesulfonyl chloride (470 g, 4.1 mol) was added dropwise over 3 hours. The reaction mixture was stirred an additional 3 hours while warming to 25° C., then water (1,000 mL) was added and the phases were separated. The organic layer was washed with ice-cold 6 N HCl (2×1,000 mL) and then washed with 5% Na$_2$CO$_3$, saturated aqueous NaCl, dried, filtered and evaporated in vacuo to yield 627 g (90%) of tetraethylene glycol dimesylate, i.e.,

$$CH_3SO_2-O-(CH_2CH_2O)_4SO_2CH_3$$

as an analytically pure, amber oil: NMR (CDCl$_3$), 3.0 (s, 6H), 3.5–4.0 (m, 12H), 4.3–4.5 (m, 4H); IR 3030, 2940–2880 (s), 1450, 1350 (s), 1170 (s), 1140 (s), 1110 (s), 1020 (s), 970 (s), 920 (s), 800 (s), 730 cm$^{-1}$.

Anal. Calcd for C$_{10}$H$_{22}$O$_9$S$_2$: C, 34.28; H, 6.33; S, 18.30. Found: C, 33.98, H, 6.50; S, 18.00.

N-Allylmonoaza-18-Crown-6 Preparation

A 5,000 mL, 3-necked flask equipped with a mechanical stirrer, reflux condenser and 500 mL addition funnel was charged with sodium hydride (50.4 g, 1.05 mol). The mineral oil in the sodium hydride was removed by washing with hexanes (4×20 mL) and syringing the spent solvent from the flask. THF (2,000 mL) was added and the resulting mixture stirred and heated to reflux. A mixture of N-allyldiethanolamine (73 g, 0.50 mol) and tetraethylene glycol dimesylate (175 g, 0.50 mol) was diluted with THF to a volume of 500 mL. The mixture was added to the NaH suspension over several hours and the reaction mixture was stirred an additional 24 hours at reflux. The THF was distilled from the reaction vessel leaving behind a slurry of crude crown and salts. Water (1,500 mL) was added to dissolve the salts, and the resulting solution was left basic. The alkaline, aqueous mixture was extracted with dichloromethane (2×1,000 mL), then the organic solution was dried and reduced in vacuo to leave 109 g of crude oily crown. The residue was chromatographed on alumina (5.5×30 cm) with 0–5% v/v 2-propanol/petroleum ether (bp 35°–60° C.) to yield 58 g (38%) of pure N-allylmonoaza-18 crown-6, i.e.,

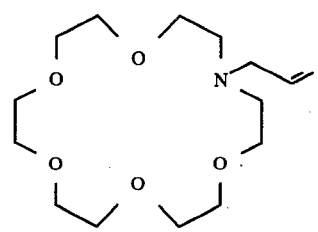

NMR (CDCl$_3$, delta) 2.6–2.9 (t, 4H), 3.1–3.25 (d, 2H), 2.5–3.8 (bs, 20H), 4.9–5.3 (m, 2H), 5.6–6.3 (bm, 1H; IR (neat) 3080, 2950–2800 (s), 1640, 1450, 1420, 1350, 1290, 1250, 1130 (s), 990, 920, 840 cm$^{-1}$.

Anal. Calcd for C$_{15}$H$_{29}$NO$_5$: C, 59.38; H, 9.63; N, 4.62. Found: C, 59.12; H, 9.86; N, 4.57.

EXAMPLE 3

N-(2-Hydroxypropyl)monoaza-18-crown-6 Preparation

The title compound was prepared by oxymercuration of N-allylmonoaza-18-crown-6 (see above). Mercuric acetate (3.19 g, 10.0 mol) was placed in a 50 ml flask equipped with a condenser and thermometer. Water (10 mL) and THF (8 mL) were added. N-allylmonoaza-18-crown-6 (1.5 g) was added at once and rinsed in with 2 ml of THF. The reaction mixture was stirred for 0.5 hr. Then 3 N NaOH was added, followed by 1 M NaBH$_4$/10% NaOH (7 mL). The reaction mixture was stirred for an additional 0.5 hr., then filtered and the THF evaporated. The product was extracted with dichloromethane, dried, filtered through Celite and the solvent evaporated in vacuo. The product, i.e.,

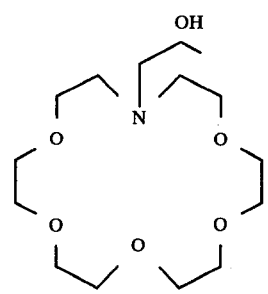

was obtained in quantitative yield as a light yellow oil.

EXAMPLE 4

N-(2-Methoxyethyl)diethanolamine Preparation

The above named compound was prepared by the procedure described in Example 1 for N-allyldiethanolamine, using 0.5 mol of diethanolamine, 0.55 mol of 2-methoxyethyl tosylate and 29.15 g of sodium carbonate. After workup the crude product was fractionally distilled and the fraction boiling from 90°–110° at 0.1 mm was collected. N-(2-Methoxyethyl)diethanolamine, i.e.,

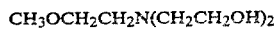

was obtained (56.6 g, 69%) as an almost colorless oil.

EXAMPLE 5

N-(2-Methoxyethyl)monoaza-15-crown-5 Preparation

A 1 liter, 3-necked, round bottomed flask, equipped with condenser and nitrogen inlet, mechanical stirrer and Claisen adapter, in which was placed a 125 mL addition funnel, was flushed with nitrogen for about 3 min. Sodium hydride (10.08 g, was added to the reaction vessel and rinsed with hexanes (4×100 mL). Freshly distilled THF (250 mL) was added and the sodium hydride slurried in it. The THF was then brought to reflux by heating with an electric mantle. N-(2-Methoxyethyl)diethanolamine (16.3 g, 0.1 mol) and triethylene glycol dimesylate (30.6 g, 0.1 mol) were combined and diluted to 100 mL volume with THF. This solution was added dropwise at reflux while stirring vigorously. Reflux was continued overnight. A small amount of water was then added and THF removed by rotary evaporation at reduced pressure. The residue was transferred to 1,000 mL separatory funnel and water (400 mL and dichloromethane (400 mL) were added. The layers were separated and the aqueous layers extracted again with another portion of dichloromethane (200 mL). The dichloromethane was then removed by rotary evaporation and the residue chromatographed over a column of alumina. Upon elution with 4% to propanol in petroleum ether N-(2-methoxyethyl)monoaza-15-crown-5, i.e.,

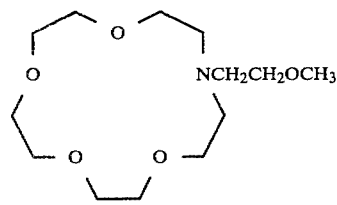

(19.0 g, 69%) was obtained.

Anal. Calcd for $C_{13}H_{27}O_5N$: N, 5.05%. Found: N, 5.13%. This compound exhibited a binding constant in aqueous solution (log Ks) of 2.52.

EXAMPLE 6

N-(2-Methoxyethyl)monoaza-18-crown-6 Preparation

The preparation of the title compound was conducted exactly as described in Example 5 above except that tetraethylene glycol dimesylate (35.0 g, 0.1 mol) was substituted for the corresponding triethylene glycol dimesylate in the procedure above. The title compound whose structure is shown below was obtained (17.0 g, 53%) as a light yellow oil after chromatography over alumina using 4% 2-propanol in petroleum ether as eluent, i.e.,

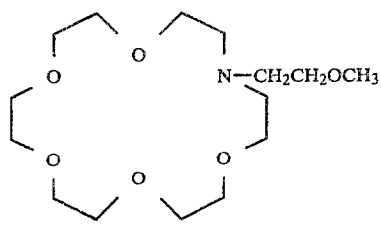

Anal. Calcd for $C_{15}H_{31}O_6N$: N, 4.36%. Found: N, 4.49%.

EXAMPLE 7

N-[2-(2-Methoxyethoxy)ethyl]diethanolamine Preparation

The title compound was prepared as described above for N-allyldiethanolamine in Example 1 except that 2-methoxyethoxyethyl tosylate was used (0.55 mol, 150.9 g) in a 0.5 mol preparation. The pure diol whose formula is shown below was obtained (49.8 g, 48%) on fractional distillation at 129°–131° C. (0.04 mm):

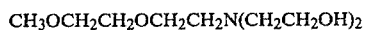

EXAMPLE 8

N-[2-(2-Methoxyethoxy)ethyl]monoaza-15-crown-5 Preparation

The title compound whose structure is shown below was prepared on a 0.1 mol scale by the method described above for N-(2-methoxyethyl)monoaza-15-crown-5 (Example 5). After chromatography over alumina, (4% 2-propanol/petroleum ether) N-[2-(2-methoxyethoxy)ethyl]-monoaza-15-crown-5 was obtained (15.1 g, 47% yield). The product appeared from chromatographic and NMR analysis to be pure:

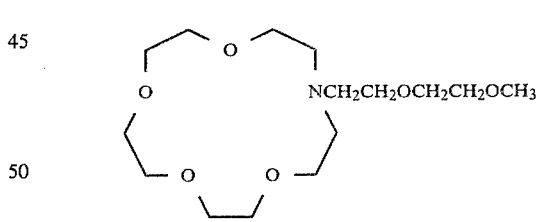

EXAMPLE 9

N-[2-(2-Methoxyethoxy)ethyl]monoaza-18-crown-6 Preparation

The title compound whose structure is shown below was prepared by the method described above for N-allyl-monoaza-18 crown-6 (Example 2) on a 0.1 mol scale. After chromatography over alumina (4% 2-propanol/petroleum ether) N-[2-(2-methoxyethoxy)ethyl]monoaza-18-crown-6 (18.1 g, 50%) was obtained as a yellow hygroscopic oil. NMR, IR and gas chromatographic analysis showed the compound to be pure, i.e.,

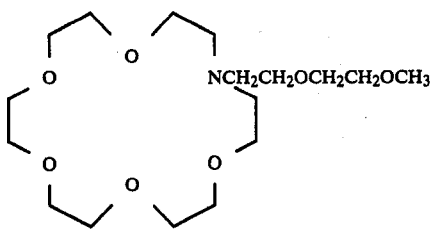

EXAMPLE 10

N-(3,6,9-Trioxadecyl)monoaza-15-crown-5

Monoaza-15-crown-5, obtained by hydrogenolysis of the corresponding N-benzyl crown as described in Gokel, G. W.; and Garcia, B. J.; *Tetrahedron Letters,* 1977, 317 (0.08 mol), $Na_2CO_3$ (0.08 mol) and freshly distilled THF (200 mL) were heated to reflux. A solution of 3,6,9-trioxadecyl tosylate (0.08 mol) in THF (50 ml) was added dropwise. Reflux was continued overnight and then the reaction mixture was cooled, filtered and the solvent evaporated. The residue was extracted with water (200 mL) and $CH_2Cl_2$ (2×200 mL). The solvent was evaporated, and the material was chromatographed over alumina. Kugelrohr distillation of the chromatographed material afforded pure N-(3,6,9-trioxadecyl)-monoaza-15-crown-5, i.e.,

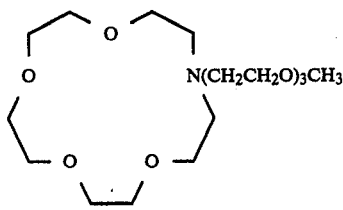

in 34% yield as a colorless oil, bp 155° C. at 0.05 torr.
Anal. Calcd for $C_{17}H_{35}O_7N$: C, 55.87; H, 9.65; N, 3.83. Found, C, 56.29; H, 9.90; N, 3.64. NMR ($CDCl_3$): 2.8 ppm (m, 6H); 3.35 ppm (s, 3H); 3.65 ppm (m, 30H).

EXAMPLE 11

N-(3,6,9-Trioxadecyl)monoaza-18-crown-6

The title compound was prepared exactly as described in the procedure of Example 10 except that monoaza-18-crown-6 rather than monoaza-15-crown-5 was used. Kugelrohr distillation of the chromatographed material afforded pure N-(3,6,9-trioxadecyl)-monoaza-18-crown-6, i.e.,

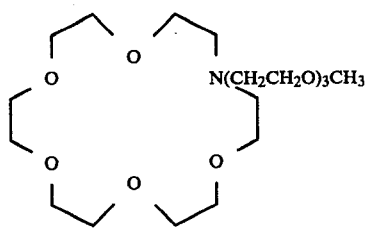

in 16% yield as a colorless oil, bp 173° C. at 0.1 torr.
Anal. Calcd. for $C_{19}H_{39}O_8N$: C, 55.73; H, 9.60; N, 3.42. Found: C, 55.45; H, 9.65; N, 3.69. NMR ($CDCl_3$): 2.8 ppm (m, 6H); 3.35 ppm (s, 3H); 3.65 ppm (m, 30H).

EXAMPLE 12

N-(3,6,9,12-Tetraoxatridecyl)monoaza-15-crown-5

The title compound was prepared exactly as described in the procedure of Example 10 except that 3,6,9,12-tetraoxatridecyl tosylate rather than 3,6,9-trioxadecyl tosylate was used. Kugelrohr distillation of the chromatographed material afforded pure N-(3,6,9,12-tetraoxatridecyl)monoaza-15-crown-5, i.e.,

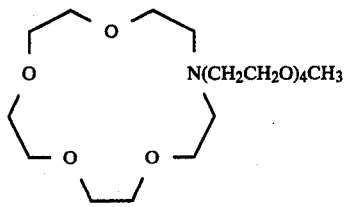

in 55% yield as a colorless oil, bp 175° C. at 0.075 torr.
Anal. Calcd for $C_{19}H_{39}O_8N$: C, 55.73;; H, 9.60;; N, 3.42. Found: C, 56.00; H, 9.86; N, 3.65; NMR ($CDCl_3$): 2.8 ppm (m, 6H); 3.4 ppm (s, 3H); 3.65 ppm (m, 30H).

EXAMPLE 13

N-(3,6,9,12-Tetraoxatridecyl)monoaza-18-crown-6

The title compound was prepared exactly as described in the procedure of Example 12 except that monoaza-18-crown-6 rather than monoaza 15-crown-5 was used. Kugelrohr distillation of the chromatographed material afforded pure N-(3,6,9,12-tetraoxatridecyl)monoaza-18-crown-6, i.e.,

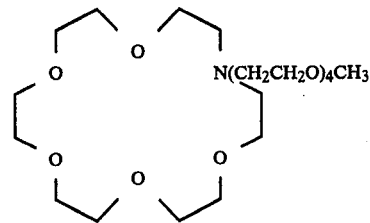

in 18% yield as a colorless oil, bp 192° C. at 0.15 torr.
Anal. calcd. for $C_{21}H_{43}O_9N$: C, 55.61; H, 9.56; N, 3.09. Found: C, 55.50; H, 9.80; N, 3.05. NMR ($CDCl_3$): 2.8 ppm (m, 6H); 3.4 ppm (s, 3H); 3.65 ppm (m, 34H).

General Procedure for the Preparation of N-Substituted Monoaza-12-crown-4 Compounds (Method A)

A 1,000 mL, 3-necked, roundbottomed flask was equipped with a mechanical stirrer, a reflux condenser and a serum cap. The reaction was carried out under an $N_2$ atmosphere. Into the flask were placed $Na_2CO_3$ (26.5 g, 0.25 mol), 1,11-diiodo-3,6,9-trioxundecane (20.7 g, 0.05 mol) and $CH_3CN$ (400 mL). This mixture was stirred and heated to reflux. The primary amine (0.05 mol) was dissolved in $CH_3CN$ (ca. 25 mL). This solution was placed in a syringe which was coupled to a length of Teflon microtubing with a Lauer fitting. The tubing was threaded through the serum cap. The syringe was placed on a Sage Instruments model 341A syringe pump. The amine was then added in a dropwise fashion over a ca. 5 hour-period. The mixture was then stirred for an additional 24–48 hours at reflux. It was then allowed to cool and was filtered. The filtrate was concentrated. The residue was stirred with CH₂Cl₂ and filtered to remove the residual NaI. The crude product was purified by Kugelrohr distillation.

EXAMPLE 14

Preparation of N-(2-Methoxyphenyl)monoaza-12-crown-4

The title compound:

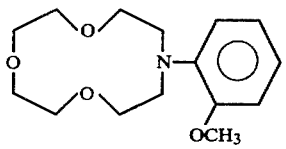

was prepared as described in the general procedure of Method A in 29% yield (bp 138°–143° C. @ 0.03 torr) from 2-methoxyaniline. NMR δ (CDCl₃) 3.30 (m, 4H); 3.67 (m, 15H); 6.90 (m, 4H). IR 3060, 2850, 1595, 1500, 1460, 1360, 1240, 1130 (s), 1025, 975, 930, 910, 830, 745 cm⁻¹. The ultraviolet spectrum of cobalt nitrate in the absence and presence of the compound of Example 14 was shifted from 512 nm to 505 nm indicative of binding between the two species.

EXAMPLE 15

Preparation of N-(2-Methoxybenzyl)monoaza-12-crown-4

The title compound, i.e.,

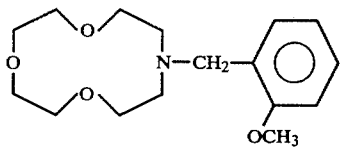

was prepared as described in the general procedure of Method A from 2-methoxybenzylamine in 32% yield (bp 150°–153° C. @ 0.03 torr). NMR δ 2.77 (t, 4H), 3.67 (m, 17H), 7.13 (m, 4H). IR 3060, 2840, 1600, 1585, 1490, 1460, 1360, 1285, 1240, 1130 (s), 1030, 910, 835, 750, 710 cm⁻¹.

Anal. calcd. for C₁₆H₂₅NO₄: C, 65.06; H, 8.53; N, 4.74. Found: C, 64.97; H, 8.63; N, 4.50.

The ultraviolet spectrum of cobalt nitrate in the absence and presence of the compound of Example 15 was shifted from 512 nm to 633 nm indicative of binding between the two species.

EXAMPLE 16

Preparation of N-(2-Dimethylaminoethyl)monoaza-12-crown-4

The title compound, i.e.,

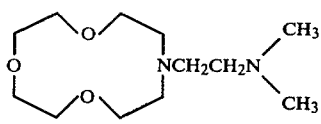

was prepared as described in the general procedure of Method A from N,N-dimethylethylenediamine in 21% yield (bp 85°–90° C. @ 0.05 torr). NMR δ 2.13 (s, 6H); 2.54 (m, 8H); 3.60 (m, 12H). IR 2940, 2850, 1460, 1360, 1290, 1260, 1130 (s), 1040, 920, 860, 840 cm⁻¹.

Anal. calcd. for C₁₂H₂₆N₂O₃: C, 58.51; H, 10.64; N, 11.37. Found: C, 58.57; H, 10.96; N, 11.12.

The ultraviolet spectrum of cobalt nitrate in the absence and presence of the compound of Example 16 was shifted from 512 nm to 644 nm indicative of binding between the two species.

I claim:

1. An ether composition of the formula:

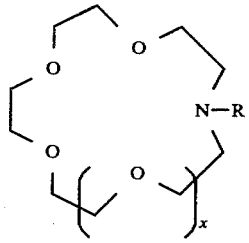

where
x is 0, 1 or 2 and
R is
2-(alkoxy)$_q$alkyl-,
2-alkoxy phenyl-,
2-alkoxy phenylmethyl-,
2-alkoxy phenylethyl-,
amino alkyl-, or
2-amino phenyl-, wherein q is 1 to 4, the alkoxy and alkyl groups contain 1 to 3 carbon atoms, the said amino is NH₂—, monoalkylamino- or dialkylamino-, wherein the alkyl on the amino contains 1 to 2 carbon atoms and wherein the said 2-alkoxy phenyl rings may optionally be substituted by up to two alkyl and/or alkoxy groups, each of 1 to 3 carbon atoms.

2. The composition according to claim 1 wherein the ether is N-(2-methoxyethyl)monoaza-15-crown-5.

3. The composition according to claim 1 wherein the ether is N-(2-methoxyethyl)monoaza-18-crown-6.

4. The composition according to claim 1 wherein the ether is N-[2-(2-methoxyethoxy)ethyl]monoaza-15-crown-5.

5. The composition according to claim 1 wherein the ether is N-[2-(2-methoxyethoxy)ethyl]monoaza-18-crown-6.

6. The composition according to claim 1 wherein the ether is N-(3,6,9-trioxadecyl)monoaza-15-crown-5.

7. The composition according to claim 1 wherein the ether is N-(3,6,9-trioxadecyl)monoaza-18-crown-6.

8. The composition according to claim 1 wherein the ether is N-(3,6,9,12-tetraoxatridecyl)monoaza-15-crown-5.

9. The composition according to claim 1 wherein the ether is N-(3,6,9,12-tetraoxatridecyl)monoaza-18-crown-6.

10. The composition according to claim 1 wherein the ether is N-(2-methoxyphenyl)monoaza-12-crown-4.

11. The composition according to claim 1 wherein the ether is N-(2-methoxybenzyl)monoaza-12-crown-4.

12. The composition according to claim 1 wherein the ether is N-(2-dimethylaminoethyl)monoaza-12-crown-4.

* * * * *